US009243210B2

(12) United States Patent
Chapuis

(10) Patent No.: US 9,243,210 B2
(45) Date of Patent: Jan. 26, 2016

(54) VIOLET LEAVES ODORANTS

(71) Applicant: FIRMENICH SA, Geneva (CH)

(72) Inventor: Christian Chapuis, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/801,767

(22) Filed: Jul. 16, 2015

(65) Prior Publication Data

US 2015/0322375 A1 Nov. 12, 2015

Related U.S. Application Data

(62) Division of application No. 14/237,939, filed as application No. PCT/EP2012/063765 on Jul. 13, 2012, now Pat. No. 9,115,329.

(30) Foreign Application Priority Data

Aug. 11, 2011 (EP) .................................... 11177220

(51) Int. Cl.

| | |
|---|---|
| ***A61K 8/00*** | (2006.01) |
| ***C11B 9/00*** | (2006.01) |
| ***C11D 3/00*** | (2006.01) |
| ***C11D 3/18*** | (2006.01) |
| ***C11D 3/50*** | (2006.01) |
| ***C11D 3/16*** | (2006.01) |

(52) U.S. Cl.

CPC .............. *C11B 9/0007* (2013.01); *C11D 3/001* (2013.01); *C11D 3/164* (2013.01); *C11D 3/184* (2013.01); *C11D 3/50* (2013.01)

(58) Field of Classification Search

CPC ....................................................... C11B 9/007
USPC .............................................................. 512/1
See application file for complete search history.

(56) References Cited

U.S. PATENT DOCUMENTS

| | | | |
|---|---|---|---|
| 3,970,592 | A | 7/1976 | Ploner |
| 5,538,943 | A | 7/1996 | Naef et al. |

FOREIGN PATENT DOCUMENTS

| | | |
|---|---|---|
| EP | 0 694 604 A2 | 1/1996 |
| EP | 1 784 374 B1 | 5/2007 |
| WO | 2006/021857 | 3/2006 |

OTHER PUBLICATIONS

Appl. No. PCT/EP2012/063765, International Search Report and Written Opinion, Oct. 5, 2012.
Bromatologia i Chemia Toksykologiczna, 25: 267 (1992).
Bosshardt et al., Helvetica Chimica Acta, 63 (8): 2393-403 (1980).
Danehy et al., J. Am. Chem. Soc., 58 (4): 611-612 (1936).
U.S. Appl. No. 14/237,939, Notice of Allowance, May 26, 2015.

*Primary Examiner* — John Hardee
(74) *Attorney, Agent, or Firm* — Winston & Strawn LLP

(57) ABSTRACT

A method of use, as a perfuming ingredient, of a compound of formula I (I)

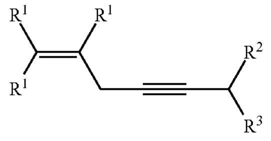

in the form of any one of its stereoisomers or a mixture thereof, and wherein each $R^1$ represents a hydrogen atom or a methyl group and at least one of said $R^1$ is a hydrogen atom; $R^2$ represents a linear or branched $C_{3-8}$ alkyl group or unsaturated groups; and $R^3$ represents a hydrogen atom or a methyl group. These compounds impart odor notes of the violet leaves type optionally together with green odor notes.

9 Claims, No Drawings

VIOLET LEAVES ODORANTS

CROSS-REFERENCE TO RELATED APPLICATIONS

This application is a division of U.S. application Ser. No. 14/237,939 filed Feb. 10, 2014, now U.S. Pat. No. 9,115,329, which is a 371 filing of International application no. PCT/EP2012/063765 filed Jul. 13, 2012, which claims priority to European application no. 11177220.8 filed Aug. 11, 2011.

TECHNICAL FIELD

The present invention relates to the field of perfumery. More particularly, it concerns the use as perfuming ingredient of a compound of formula (I), as defined below, in particular to confer odor notes of the violet leaves type. Moreover, following what is mentioned herein, the present invention comprises the invention's compound as part of a perfuming composition or of a perfuming consumer product.

PRIOR ART

The perfumery industry is always searching for new ingredients allowing new possibilities in the accord generation and also rendering the formulation easier and safer. This is also valid for the family of the violet odorant, an important class of ingredients.

Although several compounds of formula (I) have been described in the prior art, in general as simple chemicals, none of the invention's compound has been described as having organoleptic properties, and furthermore none has been suggested as odorant ingredient. For example one may cite the following prior art citations:

- dodec-2-en-5-yne is disclosed, in Bromatologia i Chemia Toksykologiczna, 1992, 25, 267, as being part of the volatile fraction of krill products but no odor or organoleptic properties are described or suggested;
- dec-1-en-4-yne is disclosed, in Helv. Chim. Acta, 1980, 63, 2393-403, as a chemical intermediate and no odor or organoleptic properties are described or suggested;
- dec-1-en-4-yne, undec-1-en-4-yne and non-1-en-4-yne are disclosed, in J.A.C.S, 1936, 58, 611, as chemical intermediates and no odor or organoleptic properties are described or suggested.

From a structural point of view, the closest known perfuming ingredient is 1,3-undecadien-5-yne disclosed in EP 694604 as having a floral, green galbanum odor, which is an odor type of the same olfactive family of the present invention's compounds. However, said prior art compound possesses a chemical structure quite different, by having an additional ethylene group and by being a fully conjugated compound. By no means said prior art document suggests the organoleptic properties of the present invention's compounds.

Alternatively, other structurally related perfuming ingredients are the ones disclosed in EP 1784374, having also an odor type of the same olfactive family of the present invention's compounds. However, said prior art compounds possess a chemical structure quite different for the same reason as for the previous prior art document plus comprise also an ether functional group. By no means said prior art documents suggest the organoleptic properties of the present invention's compounds.

DESCRIPTION OF THE INVENTION

We have now surprisingly discovered that a compound of formula (I)

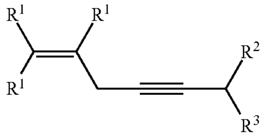

in the form of any one of its stereoisomers or a mixture thereof, and wherein each $R^1$ represents a hydrogen atom or a methyl group and at least one of said $R^1$ is a hydrogen atom;

$R^2$ represents a linear or branched $C_{3-8}$ alkyl group or unsaturated groups; and $R^3$ represents a hydrogen atom or a methyl group;

can be used as perfuming ingredient, for instance to impart odor notes of the violet leaves type optionally together with green odor notes.

For the sake of clarity, by the expression "unsaturated group", or the similar, it is meant the normal meaning understood by a person skilled in the art, i.e. an alkynyl, alkynyl or alkenynyl (a group comprising a carbon-carbon double bond and a carbon-carbon triple bond, and in the present invention preferably not being conjugated) group.

According to an embodiment of the invention, each $R^1$ represents a hydrogen atom or a methyl group and at least two of said $R^1$ are a hydrogen atom.

According to any one of the above embodiments of the invention, said compound (I) is a compound of formula (II)

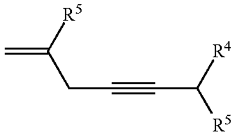

wherein $R^4$ represents a linear or branched $C_{4-7}$ alkyl group or unsaturated groups; and each $R^5$ represents a hydrogen atom or a methyl group.

According to an embodiment of formula (II), at least one $R^5$ represents a hydrogen atom, or even both $R^5$ are hydrogen atoms.

According to any one of the above embodiments of the invention, said $R^4$ or $R^2$ represents a linear $C_{3-7}$ alkyl group or unsaturated group. Or said $R^4$ or $R^2$ represents a linear $C_{3-7}$ alkyl group.

According to any one of the above embodiments of the invention, said $R^4$ or $R^2$ represents a linear group.

According to any one of the above embodiments of the invention, said compounds (I) are $C_9$-$C_{13}$ compounds, or even $C_{10}$-$C_{12}$ compounds.

As specific examples of the invention's compounds, one may cite, as non-limiting example, dec-1-en-4-yne which possesses an odor characterized by green/galbanum and violet leaves notes as well as having a fruity/pear and truffle aspect. It can be said that this invention's compound reminds of the odor of methyl octane carbonate or methyl heptyl carbonate, known as perfect violet odorant but now limited or not used for various reasons.

The odor of dec-1-en-4-yne when compared to the one of the prior art 1,3-undecadien-5-yne differs by having stronger and fresher galbanum, truffle and pear aspects as well as by having a substantivity/performance which is about twice the one of the prior art compounds. Furthermore it was also noted that the present compound is much more stable (from a chemical point of view) in the standard perfumery media.

As other example, one may cite dodeca-1,11-dien-4,8-diyne, which possesses an odor characterized green/galbanum and violet leaves notes, as the above compound, but has also an interesting lavender aspect. Said compound is more galbanum than the above mentioned dec-1-en-4-yne and also possesses an aromatic aspect absent in the latter (as well as absent in 1,3-undecadien-5-yne).

As other specific, but non-limiting, examples of the invention's compounds, one may cite the following ones in Table 1:

TABLE 1

Invention's compounds and their odor properties

| Compound structure and name | Odor notes |
|---|---|
| 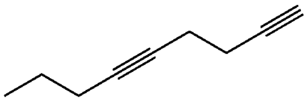 nona-1-en-4,8-diyne | green, violet leaves, acetylene |
| 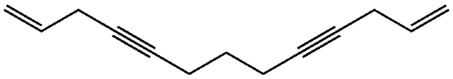 trideca-1,12-dien-4,9-diyne | galbanolene, acetylene, pear, violet leaves, reminding of methyl octane carbonate |
| 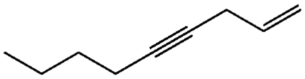 non-1-en-4-yne | green, foliage, violet leaves, acetylene |
| 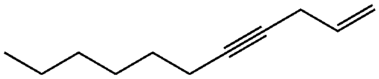 undec-1-en-4-yne | nice, violet leaves |
| 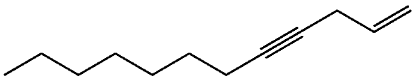 dodec-1-en-4-yne | violent leaves, pear, acetylene |
| 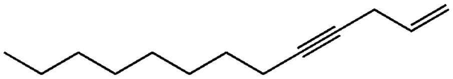 tridec-1-en-4-yne | green, violent leaves, |
| 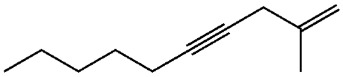 2-methyldec-1-en-4-yne | violent leaves, earthy, cellar |
| 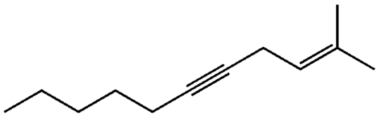 2-methylundec-2-en-5-yne | green, violent leaves, metallic, acetylene |
| 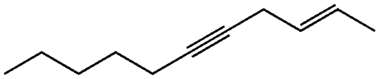 undec-2-en-5-yne | green, violet leaves, acetylene |

According to a particular embodiment of the invention, the compounds of formula (I) are dec-1-en-4-yne, dodeca-1,11-dien-4,8-diyne, trideca-1,12-dien-4,9-diyne, non-1-en-4-yne, undec-1-en-4-yne, dodec-1-en-4-yne or 2-methyldec-1-en-4-yne.

When the odor of the invention's compounds is compared with that of the prior art commercial compounds (in particular 1,3-undecadien-5-yne), then the invention's compounds distinguish themselves by a clearly stronger green/galbanum and in some cases by having additional olfactive aspects (such as earthy or aromatic ones) and also by being more substantive.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one compound of formula (I), as defined above; and
ii) a perfumery consumer base;

is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the compounds of the invention based on the weight of the composition into which they are incorporated. Concentrations lower than these, such as in the order of 0.01% to 1% by weight, can be used when these compounds are incorporated into perfumed articles, percentage being relative to the weight of the article.

The invention's compounds can be prepared according to a method as described in the Examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts 8 are indicated in ppm with respect to TMS as standard, the coupling constants J are expressed in Hz.

Example 1

Synthesis of Compounds of Formula (I)

a) Synthesis of dec-1-en-4-yne

A solution of bromoethane (43.6 g, 400 mmol) in $Et_2O$ (280 ml) was added dropwise to a suspension of Mg (9.6 g, 400 mmol) in $Et_2O$ (140 ml). After 3 hours a solution of 1-heptyne (35.0 g, 360 mmol) in $Et_2O$ (140 ml) was added dropwise to the reaction medium. After 90 minutes at reflux, CuCl (1.8 g, 18.2 mmol) was added to the cold reaction mixture and after 15 minutes a solution of allyl bromide (48.4 g, 400 mmol) in $Et_2O$ (140 ml) was added dropwise. After 18 hours at reflux, the cold reaction mixture was poured onto 10% aqueous HCl (320 ml) at 0° C. The aqueous phase was extracted with $Et_2O$, then the organic phase was washed with $H_2O$, dried ($MgSO_4$), concentrated and distilled through a Vigreux column (65915 mbar) to afford the pure desired compound (70%).

$^1H$-NMR: 0.89 (t, J=7, 3H); 1.25-1.34 (m, 2H); 1.38-1.42 (m, 2H); 1.50 (quint, J=7, 2H); 2.18-2.21 (m, 2H); 2.92-2.96 (m, 2H); 5.09 (dq, J=2, 11, 1H); 5.32 (dq, J=2, 16, 1H); 5.77-5.89 (m, 1H).

$^{13}C$-NMR: 133.5 (d); 115.5 (t); 82.9 (s); 76.5 (s); 31.2 (t); 28.8 (t); 23.2 (t); 22.3 (t); 18.8 (t); 14.0 (s).

b) Synthesis of undec-1-en-4-yne

Obtained in 80% yield from 1-octyne according to the procedure described under a).

Bp: 80°/1.6 mbar.

$^1H$-NMR: 0.89 (t, J=7, 3H); 1.25-1.34 (m, 4H); 1.38-1.42 (m, 2H); 1.50 (quint, J=7, 2H); 2.18-2.21 (m, 2H); 2.92-2.96 (m, 2H); 5.09 (dq, J=2, 11, 1H); 5.32 (dq, J=2, 16, 1H); 5.77-5.89 (m, 1H).

$^{13}C$-NMR: 133.4 (d); 115.6 (t); 82.9 (s); 76.5 (s); 31.4 (t); 29.1 (t); 28.6 (t); 23.2 (t); 22.6 (t); 18.8 (t); 14.1 (q).

c) Synthesis of dodec-1-en-4-yne

Obtained in 60% yield from 1-nonyne according to the procedure described under a).

Bp: 80°/1.4 mbar.

$^1H$-NMR: 0.89 (t, J=7, 3H); 1.28-1.34 (m, 6H); 1.34-1.42 (m, 2H); 1.51 (quint, J=7, 2H); 2.17-2.21 (m, 2H); 2.92-2.97 (m, 2H); 5.09 (dq, J=2, 11, 1H); 3.32 (dq, J=2, 16, 1 H); 5.79-5.89 (m, 1H).

$^{13}C$-NMR: 133.4 (d); 115.6 (t); 83.0 (s); 76.5 (s); 31.8 (t); 29.1 (t); 28.9 (2t); 23.2 (t); 22.7 (t); 18.8 (t); 14.1 (q).

d) Synthesis of trideca-1,12-dien-4,9-diyne

Obtained in 80% yield from hepta-1,6-diyne according to the procedure described under a) but using twice the quantity of allyl reagents.

Bp: 85°/0.36 mbar.

$^1H$-NMR: 1.72 (quint, J=7, 2H); 2.28-2.34 (m, 4H); 2.92-2.96 (m, 4H); 5.09 (dq, J=2, 11, 1H); 5.31 (dq, J=2, 16, 1H); 5.79-5.88 (m, 1H).

$^{13}$C-NMR: 133.3 (2d); 115.6 (2t); 81.8 (2s); 77.2 (2s); 28.5 (t); 23.1 (2t); 18.0 (2t).

e) Synthesis of nona-1-en-4,8-diyne

Obtained in 63% yield from hexa-1,5-diyne to the procedure described under a).

Bp: 90°/1.5 mbar.

$^{1}$H-NMR: 2.02 (t, J=2, 1H); 2.38-2.47 (m, 4H); 2.93-2.97 (m, 2H); 5.10 (dq, J=2, 11, 1H); 5.33 (dq, J=2, 16, 1H); 5.77-5.88 (m, 1H).

$^{13}$C-NMR: 133.0 (d); 115.8 (t); 83.0 (s); 80.8 (s); 77.9 (s); 69.1 (d); 23.1 (t); 19.1 (t); 18.9 (t).

f) Synthesis of dodeca-1,11-dien-4,8-diyne

Obtained in 61% yield from nona-1-en-4,8-diyne according to the procedure described under d).

Bp: 90°/0.05 mbar.

$^{1}$H-NMR: 2.42 (t, J=1, 4H); 2.93-2.97 (m, 4H); 5.09 (dq, J=2, 11, 2H); 5.35 (dq, J=2, 16, 2H); 5.79-5.86 (m, 2H).

$^{13}$C-NMR: 133.1 (2d); 115.8 (2t); 81.3 (s); 77.6 (2s); 23.1 (2t); 19.4 (2t).

g) Synthesis of non-1-en-4-yne

Obtained in 76% yield from 1-hexyne according to the procedure described under a).

Bp: 60°/18 mbar.

$^{1}$H-NMR: 0.91 (t, J=7, 3H); 1.38-1.54 (m, 4H); 2.16-2.22 (m, 2H); 2.92 2.96 (m, 2H); 5.09 (dt, J=1.8, 9.9, 1H); 5.32 (dq, J=1.8, 16.7, 1H); 5.78-5.87 (m, 1H). $^{13}$C-NMR: 133.4 (d); 115.5 (t); 82.8 (s); 76.4 (s); 31.2 (t); 22.0 (t); 18.5 (t); 13.6 (q).

h) Synthesis of tridec-1-en-4-yne

Obtained in 66% yield from 1-decyne according to the procedure described under a).

Bp: 80°/6.6 mbar.

$^{1}$H-NMR: 0.89 (t, J=7, 3H); 1.14-1.31 (m, 6H); 1.36-1.43 (m, 2H); 1.47-1.54 (m, 2H); 2.16-2.21 (m, 2H); 2.92-2.95 (m, 2H); 5.09 (dq, J=1.8, 10, 1H); 5.38 (dq, J=1.8, 17, 1H); 5.77-5.86 (m, 1H).

$^{13}$C-NMR: 133.4 (d); 115.6 (t); 82.9 (s); 76.5 (s); 31.9 (t); 29.2 (2t); 29.1 (t); 28.9 (t); 23.2 (t); 22.7 (t); 18.8 (t); 14.1 (q).

i) Synthesis of 2-methyl-dec-1-en-4-yne

Obtained quantitatively from 1-heptyne using methallylchloride according to the procedure described under a).

Bp: 70°/4.2 mbar.

$^{1}$H-NMR: 0.90 (t, J=7, 3H); 1.28-1.41 (m, 4H); 1.48-1.56 (m, 2H); 1.78 (s, 3H); 2.15-2.21 (m, 2H); 2.87 (s, 2H); 4.82 (s, 1H); 5.00 (s, 1H).

$^{13}$C-NMR: 141.4 (s); 111.2 (t); 82.8 (s); 77.0 (s); 31.1 (t); 28.8 (t); 27.6 (t); 22.2 (t); 22.0 (q); 18.8 (t); 14.0 (q).

j) Synthesis of 2-methylundec-2-en-5-yne

Obtained in 77% yield from 1-heptyn using 1-chloro-3-methylbut-2-ene and using methallylchloride according to the procedure described under a).

Bp: 70°/3.7 mbar.

$^{1}$H-NMR: 0.90 (t, J=7, 3H); 1.28-1.38 (m, 4H); 1.45-1.51 (m, 2H); 1.62 (s, 3H); 1.71 (s, 3H); 2.14 (tt, J=2.6, 7, 2H); 2.86 (brd, J=7, 2H); 5.18 (thept, J=1.5, 7, 1H).

$^{13}$C-NMR: 133.2 (s); 120.0 (d); 79.9 (s); 78.8 (s); 31.1 (t); 28.8 (t); 25.5 (q); 22.3 (t); 18.8 (t); 17.9 (t); 17.6 (q); 14.0 (q).

k) Synthesis of (E)-undec-2-en-5-yne

Obtained in 74% yield (as a 92:8 E/Z mixture) from 1-heptyn using 1-bromo-but-2-en and using methallylchloride according to the procedure described under a).

Bp: 70°/5 mbar.

$^{1}$H-NMR: 0.90 (t, J=7, 3H); 1.29-1.40 (m, 4H); 1.47-1.54 (m, 2H); 1.68 (dq, J=1.5, 6.5, 3H); 2.14-2.20 (m, 2H); 2.85-2.88 (m, 2H); 5.39-5.46 (m, 1H); 5.63-5.72 (m, 1H).

$^{13}$C-NMR: (E) 126.3 (d); 126.0 (d); 82.1 (s); 77.5 (s); 31.2 (t); 28.8 (t); 22.3 (t); 22.0 (t); 18.8 (t); 17.6 (q); 14.0 (q).

Example 2

Preparation of a Perfuming Composition

A perfuming composition for softener, of the floral type, was prepared by admixing the following ingredients:

| Parts by weight | Ingredient |
|---|---|
| 100 | Benzyl acetate |
| 20 | Anisic aldehyde |
| 140 | Hexylcinnamic aldehyde |
| 10 | Methyl anthranilate |
| 50 | Dihydromyrcenol |
| 20 | Diphenyloxyde |
| 100 | Hedione ® [1)] |
| 40 | Helvetolide ® [2)] |
| 30 | Ionone Alpha |
| 100 | Lilial ® [3)] |
| 20 | 10%* Gamma nonalactone |
| 50 | Phenylhexanol |
| 10 | 2-Benzyl-4,4,6-trimethyl-1,3-dioxane |
| 150 | Amyl salicylate |
| 100 | Terpineol |
| 20 | Tuberose oil |
| 20 | 10%* Vanilline |
| 980 | |

*in dipropyleneglycol 1) methyl dihydrojasmonate; origin: Firmenich SA, Geneva, Switzerland 2) (1S,1'R)-2-[1-(3',3'-dimethyl-1'-cyclohexyl)ethoxy]-2-methylpropyl propanoate; origin: Firmenich SA, Geneva, Switzerland 3) 3-(4-tert-butylpbenyl)-2-methylpropanal; origin: Givaudan SA, Vernier, Switzerland The addition of 20 parts by weight of a 10% solution of dec-1-en-4-yne in dipropyleneglycol to the above-described composition imparted to the latter a strong natural violet leaves effect, very similar to the addition of the same amount of methyl octyl carbonate (an ingredient hedonically very appreciated but restricted in use by legislation).

The addition of the same amount of the prior art 1,3-undecadien-5-yne imparted a similar effect although clearly weaker, less galbanum and less natural.

Example 3

Preparation of a Perfuming Composition

A perfume, of the green floral type, was prepared by admixing the following ingredients:

| Parts by weight | Ingredient |
|---|---|
| 100 | Benzyl acetate |
| 100 | Hexylcinnamic aldehyde |
| 5 | Methyl anthranilate |
| 60 | Bergamote essential oil |
| 30 | Citronellol |
| 30 | 10%* Dorinone ® [1)] Beta |
| 15 | Eugenol |
| 80 | Florol ® [2)] |
| 10 | Geranium essential oil |
| 100 | Hedione ® [3)] HC |
| 5 | 1,3-Benzodioxole-5-carbaldehyde |
| 60 | Helvetolide ® [4)] |
| 50 | Iralia ® [5)] |
| 15 | 10%* Isobutylquinoleine |
| 30 | Jasmin essential oil |
| 80 | Lilial ® [6)] |
| 25 | 10%* Gamma nonalactone |
| 150 | Benzyl salicylate |
| 35 | 10%* Vanilline |
| 980 | |

*in dipropyleneglycol

[1)] 1-(2,6,6-trimethyl-1-cyclohexen-1-yl)-2-buten-1-one; origin: Firmenich SA, Geneva, Switzerland

[2)] tetrahydro-2-isobutyl-4-methyl-4(2H)-pyranol; origin: Firmenich SA, Geneva, Switzerland

[3)] methyl cis-dihydrojasmonate; origin: Firmenich SA, Geneva, Switzerland

[4)] (1S,1'R)-2-[1-(3',3'-dimethyl-1'-cyclohexyl)ethoxy]-2-methylpropyl propanoate; origin: Firmenich SA, Geneva, Switzerland

[5)] mixture of methylionones isomers; origin: Firmenich SA, Geneva, Switzerland

[6)] 3-(4-tert-butylphenyl)-2-methylpropanal; origin: Firmenich SA, Geneva, Switzerland The addition of 20 parts by weight of a 10% solution of dec-1-en-4-yne in dipropyleneglycol to the above-described composition imparted to the latter a natural violet leaves effect, with a green facet slightly earthy evoking the truffle.

Example 4

Preparation of a Perfuming Composition

A cologne for man, of the green floral type, was prepared by admixing the following ingredients:

| Parts by weight | Ingredient |
|---|---|
| 70 | Linalyl acetate |
| 5 | 10%* Nonadienol |
| 700 | Bergamote essential oil |
| 140 | Lemon oil |
| 50 | Coumarine |
| 95 | Dihydromyrcenol |
| 500 | 70%** Galaxolide ® [1)] |
| 5 | Clove essential oil |
| 20 | 10%* Indol |
| 50 | 10%* Ionone Beta |
| 1000 | Iso E ® [2)] Super |
| 50 | Linalol |
| 275 | Lyral ® [3)] |
| 240 | Tangerine essential oil |
| 10 | Methylionone Beta |
| 10 | Crystal Moss |
| 35 | Nutmeg essential oil |
| 120 | Hedione ® [4)] |
| 10 | Dextro trans-1-(2,2,6-trimethyl-1-cyclohexyl)-3-hexanol[5)] |
| 75 | Patchouli oil |
| 50 | Amyl salicylate |
| 200 | Sandela ® [6)] |
| 460 | Tonalide ® [7)] |
| 50 | 1%* Vanillin |
| 550 | Vertofix ® [8)] Coeur |
| 30 | 10%* 2,4-Dimethyl-3-cyclohexene-1-carbaldehyde |
| 4800 | |

-continued

*in dipropyleneglycol

**in isopropyle myristate

[1)] 1,3,4,6,7,8-hexahydro-4,6,6,7,8,8-hexamethyl-cyclopenta-g-2-benzopyrane; origin: International Flavors & Fragrances, USA

[2)] 1-(octahydro-2,3,8,8-tetramethyl-2-naphthalenyl)-1-ethanone; origin: International Flavors & Fragrances, USA

[3)] 4/3-(4-hydroxy-4-methylpentyl)-3-cyclohexane-1-carbaldehyde; origin: International Flavors & Fragrances, USA

[4)] methyl dihydrojasmonate; origin: Firmenich SA, Geneva, Switzerland

[5)]origin: Firmenich SA, Geneva, Switzerland

[6)] 5-(2,2,3-trimethyl-3-cyclopentenyl)-3-methylpentan-2-ol; origin: Givaudan SA, Vernier, Switzerland

[7)] (5,6,7,8-tetrahydro-3,5,5,6,8,8-hexamethyl-2-naphthyl)-1-ethanone; origin: Givaudan SA, Vernier, Switzerland

[8)] methyl cedryl ketone; origin: International Flavors & Fragrances, USA

The addition of 20 parts by weight of dec-1-en-4-yne to the above-described composition imparted to the latter the same violet leaves twist that is imparted by the addition of the same amount of methyl octyl carbonate (OMC). It is interesting to note that such level of OMC is about 30 times more than the maximum level recommended by legislation, and therefore with the invention's compound it is possible to obtain the same hedonic effect than OMC but with a safer ingredient.

The invention claimed is:

1. A perfuming composition comprising an odor effective amount of at least a compound of formula (I)

(I)

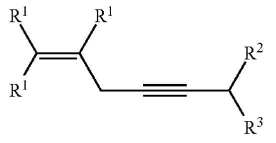

in the form of any one of its stereoisomers or a mixture thereof, and wherein each $R^1$ represents a hydrogen atom or a methyl group and at least one of said $R^1$ is a hydrogen atom;

$R^2$ represents a linear or branched $C_{3-8}$ alkyl group or unsaturated groups; and $R^3$ represents a hydrogen atom or a methyl group;

at least one ingredient selected from the group consisting of a perfumery carrier and a perfuming base to provide a hedonic effect to the composition; and at least one perfumery adjuvant for imparting an additional added benefit to the composition.

2. The composition of claim 1, wherein said compound (I) is a compound of formula (II)

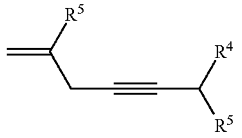

wherein $R^4$ represents a linear or branched $C_{4-7}$ alkyl group or unsaturated groups; and each $R^5$ represents a hydrogen atom or a methyl group.

3. The composition according to claim 2, wherein at least one $R^5$ represents a hydrogen atom.

4. The composition according to claim 1, wherein said $R^4$ or $R^2$ represents a linear $C_{3-7}$ alkyl, alkynyl, alkynyl or alkenynyl group.

5. The composition according to claim 1, wherein said compound is dec-1-en-4-yne, dodeca-1,11-dien-4,8-diyne, trideca-1,12-dien-4,9-diyne, non-1-en-4-yne, undec-1-en-4-yne, dodec-1-en-4-yne or 2-methyldec-1-en-4-yne.

6. The composition according to claim 1, which is present in a perfuming consumer product that includes a perfumery consumer base.

7. The composition according to claim 6, wherein the perfumery consumer base is a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a “ready to use” powdered air freshener, a wipe, a dish detergent or hard-surface detergent.

8. The composition according to claim 6, wherein said perfumery consumer base is a perfume, a fabric care product, a body-care product, an air care product or a home care product.

9. The composition according to claim 1, wherein both the perfumery carrier and perfuming base are present.

* * * * *